(12) United States Patent
Chou

(10) Patent No.: US 8,716,655 B2
(45) Date of Patent: May 6, 2014

(54) INTEGRATED ION SEPARATION SPECTROMETER

(75) Inventor: Tsung-Kuan A. Chou, San Jose, CA (US)

(73) Assignee: TricornTech Corporation, San Jose, CA (US)

( * ) Notice: Subject to any disclaimer, the term of this patent is extended or adjusted under 35 U.S.C. 154(b) by 76 days.

(21) Appl. No.: 12/828,503

(22) Filed: Jul. 1, 2010

(65) Prior Publication Data

US 2011/0001044 A1    Jan. 6, 2011

Related U.S. Application Data

(60) Provisional application No. 61/222,807, filed on Jul. 2, 2009.

(51) Int. Cl.
  *H01J 49/26* (2006.01)
  *H01J 49/04* (2006.01)
  *H01J 49/12* (2006.01)

(52) U.S. Cl.
  USPC ............................. 250/287; 250/281; 250/282

(58) Field of Classification Search
  USPC .................................. 250/281, 282, 288, 287
  See application file for complete search history.

(56) References Cited

U.S. PATENT DOCUMENTS

| 3,916,187 A * | 10/1975 | Fletcher et al. ................ 250/251 |
| 5,955,886 A | 9/1999 | Cohen et al. |
| 6,107,624 A * | 8/2000 | Doring et al. ................. 250/286 |
| 6,121,608 A | 9/2000 | Takada et al. |
| 6,225,623 B1 * | 5/2001 | Turner et al. .................... 250/286 |
| 6,509,562 B1 * | 1/2003 | Yang et al. ..................... 250/287 |
| 6,630,663 B2 * | 10/2003 | Murphy et al. ................ 250/286 |
| 6,903,331 B2 * | 6/2005 | Bateman et al. ............. 250/287 |
| 7,459,693 B2 * | 12/2008 | Park et al. ................. 250/423 R |
| 7,582,861 B2 * | 9/2009 | Mukaibatake ................ 250/281 |
| 2003/0001088 A1 * | 1/2003 | Bateman et al. ............. 250/287 |
| 2003/0070913 A1 * | 4/2003 | Miller et al. ............... 204/192.1 |
| 2003/0119193 A1 | 6/2003 | Hess et al. |
| 2005/0063865 A1 | 3/2005 | Bonne et al. |
| 2005/0156118 A1 * | 7/2005 | Chua et al. ..................... 250/426 |
| 2007/0176092 A1 * | 8/2007 | Miller et al. .................. 250/288 |
| 2007/0235643 A1 * | 10/2007 | Bonne et al. ................ 250/296 |
| 2008/0121794 A1 * | 5/2008 | Miller et al. .................. 250/282 |
| 2008/0128612 A1 * | 6/2008 | Miller et al. .................. 250/286 |
| 2008/0210861 A1 * | 9/2008 | Wu et al. ....................... 250/287 |

(Continued)

OTHER PUBLICATIONS

Chua, B., Wexler, A.S., Tien, N.C., Niemeier, D.A., Holmen, B.A. (2008) Design, Fabrication, and Testing of a Microfabricated Corona Ionizer, Journal of Microelectromechanical Systems, 17(1):115-123.*

(Continued)

*Primary Examiner* — David A Vanore
*Assistant Examiner* — Wyatt Stoffa
(74) *Attorney, Agent, or Firm* — Blakely Sokoloff Taylor & Zafman LLP

(57) ABSTRACT

An apparatus including an ion injector having an inlet and an outlet and a micro-corona ionizer positioned between the inlet and the outlet of the ion injector. A drift and separation channel having a first end and a second end is positioned with the first end coupled to outlet of the ion injector, and an ion detector is coupled to the second end of the ion separation and drift channel. Other embodiments are disclosed and claimed.

41 Claims, 11 Drawing Sheets

(56) References Cited

U.S. PATENT DOCUMENTS

| | | | |
|---|---|---|---|
| 2008/0224032 A1* | 9/2008 | Miller et al. | 250/286 |
| 2009/0014641 A1* | 1/2009 | Bateman et al. | 250/282 |
| 2009/0108193 A1 | 4/2009 | Kostiainen et al. | |
| 2009/0173877 A1* | 7/2009 | Bateman et al. | 250/282 |
| 2009/0189070 A1* | 7/2009 | Clemmer et al. | 250/282 |
| 2009/0236514 A1* | 9/2009 | Renner | 250/282 |
| 2009/0314644 A1* | 12/2009 | Golan et al. | 204/643 |
| 2010/0148053 A1* | 6/2010 | Belford et al. | 250/282 |
| 2010/0230588 A1* | 9/2010 | Atkinson et al. | 250/283 |
| 2010/0282961 A1* | 11/2010 | Miller et al. | 250/282 |
| 2010/0320375 A1* | 12/2010 | Renner | 250/282 |
| 2010/0320376 A1* | 12/2010 | Makarov et al. | 250/283 |
| 2011/0006196 A1* | 1/2011 | Boyle et al. | 250/281 |
| 2011/0006199 A1* | 1/2011 | Mattila et al. | 250/282 |
| 2011/0095175 A1* | 4/2011 | Bateman | 250/282 |
| 2011/0121170 A1* | 5/2011 | Park | 250/282 |
| 2011/0121171 A1* | 5/2011 | Clemmer et al. | 250/282 |
| 2011/0155902 A1* | 6/2011 | Guna | 250/282 |
| 2011/0220790 A1* | 9/2011 | Sun et al. | 250/288 |
| 2011/0284737 A1* | 11/2011 | Makarov et al. | 250/282 |
| 2012/0261570 A1* | 10/2012 | Shvartsburg et al. | 250/287 |
| 2013/0026357 A1* | 1/2013 | Matthews et al. | 250/282 |
| 2013/0056629 A1* | 3/2013 | Bateman et al. | 250/282 |

OTHER PUBLICATIONS

Chua, B., Wexler, A.S., Tien, N.C., Niemeier, D.A., Holmen, B.A. Design, Fabrication, and Testing of a Microfabricated Corona Ionizer, Journal of Microelectromechanical Systems, 17(1):115-123 (2008).*

Chua, B; Wexler, A.S.; Tien, N.C.; Niemeier, D.A.; Holmen, B.A.;, "Electrical Mobility Separation of Airborne Particles Using Integrated Microfabricated Corona Ionizer and Separator Electrodes," Journal of Microelectromechanical Systems, 18(1), Feb. 4-13, 2009.*

PCT/US2010/040988, International Search Report and Written Opinion of the International Searching Authority, mail date Feb. 8, 2011, 8 pages.

Fenn, John B. et al.; "Electrospray Ionization for Mass Spectrometry of Large Biomolecules," Science, vol. 246, Oct. 1989, pp. 64-71.

Miller, Raanan A. et al.; "A MEMS radio-frequency ion mobility spectrometer for chemical vapor detection," Elsevier, Sensors and Actuators A 91, 2001, pp. 301-312.

Peterson, K. A. et al.; "Novel LTCC Fabrication Techniques Applied to a Rolled Micro Ion Mobility Spectrometer," Abs. 1153, 204th Meeting, © 2003 The Electrochemical Society, Inc., 1 page.

Guevremont, R.; "High-Field Asymmetric Waveform Ion Mobility Spectrometry (FAIMS)," Canadian Journal of Analytical Sciences and Spectroscopy, vol. 49, No. 3, 2004, pp. 105-113.

Guo, Hui-yong et al.; "A novel surface ionization source for ion mobility spectrometer," Elsevier, Analytica Chimica Acta 587, 2007, pp. 137-141.

Klassen, E. H. et al., "Silicon Fusion Bonding and Deep Reactive Ion Etching: A New Technology for Microstructures", *Sensors and Actuators A 52* (1996), pp. 132-139, Elsevier Science S. A.

* cited by examiner

INTEGRATED ION SEPARATION SPECTROMETER

CROSS-REFERENCE TO RELATED APPLICATIONS

This application claims priority under 35 U.S.C. §119(e) to U.S. Provisional Patent Application No. 61/222,807, filed 2 Jul. 2009.

TECHNICAL FIELD

The present invention relates generally to gas detectors and in particular, but not exclusively, to detectors with integrated charged-ion separation.

BACKGROUND

Gas detection instruments are used to separate chemical ions from a gas and detect the ions. Existing instruments, however, all have drawbacks that make them expensive to build, burdensome to operate, and difficult or impossible to miniaturize. An Ion Mobility Spectrometer (IMS) is a gas detection instrument in which gas ions are separated according to their individual velocities as they drift through an electric field. Most traditional large non-portable IMS systems use electro-spray ionization to ionize chemical molecules, but this ionization source is too complex to be cost-effectively down-sized and integrated with other components. Other ionization techniques such as surface ionization have been used, but most of the ionization techniques require a high-vacuum environment for input sample gas, which is very challenging to be implemented in a miniature IMS system. As a result, a new ionization source that can be operated in atmospheric pressure with scalable size is necessary.

A small-scale IMS device has been reported by Sandia National Lab, but this miniature IMS drifter involves too many parts and electrical connections, which results in much lower device fabrication throughput and much higher package and assembly cost. Moreover, this IMS has a measured dimension in the range of 10 cm×2 cm×2 cm, but still needs further size reduction before it can be used as a fully-assembled handheld gas detection system.

Draper Labs developed a miniaturized Radio Frequency-IMS (rf-IMS). This rf-IMS has significant drift channel size reduction due to the simplification of the drift or separation electrodes by using High-Field Asymmetric Waveform Ion Mobility Spectrometry (FAIMS) technology to filter ions in the drift channel. Such FAIMS technology requires a very high radio frequency (RF) electric field to filter the ions in the drift channel, with a voltage of 1700V at 2 MHz frequency. The corresponding high-voltage RF power supply consumes very high power and also requires special microwave protection. Meanwhile, the electronics for producing such high voltage RF signal are very expensive and usually very large, which in turns leads to difficulty in producing a low-cost miniature gas detector system.

In both current state of the art miniature gas detection systems, radioactive materials were used as the ionization source in order to keep small system footprint: the Sandia IMS uses radioactive 241 Am as its ionization source to reduce the system size, while the Draper Labs rf-IMS uses radioactive 63Ni as the ionization source. The use of radioactive materials raises its own problems. Regular leak tests must be performed to work with such materials. Meanwhile, special safety regulations and licensing requirements can limit the commercial acceptance of devices using radioactive material. Radioactive waste disposal also raises serious concerns about environmental impacts. Therefore, the development of an ambient pressure ionization source that can replace radioactive material is desired.

Current miniature gas detectors are still constructed by separate individual components—separate ionization sources, separate ion drift and separation channels, and separate ion detector—which require significant amount of assembly efforts and thus higher cost. These separate components cannot be monolithically integrated in fabrication and require significant efforts on the assembly, which increases the device cost. A more robust miniaturized gas detector that can be inherently integrated for low-cost mass production is desirable.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified. Figures are not drawn to scale unless specifically indicated.

DETAILED DESCRIPTION OF THE ILLUSTRATED EMBODIMENTS

Embodiments of an apparatus, method and system for an integrated ion separation spectrometer are described herein. In the following description, numerous specific details are described to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail but are nonetheless encompassed within the scope of the invention.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in this specification do not necessarily all refer to the same embodiment. Furthermore, the particular features, structures, or characteristics may be combined in any suitable manner in one or more embodiments.

Figure 1A:
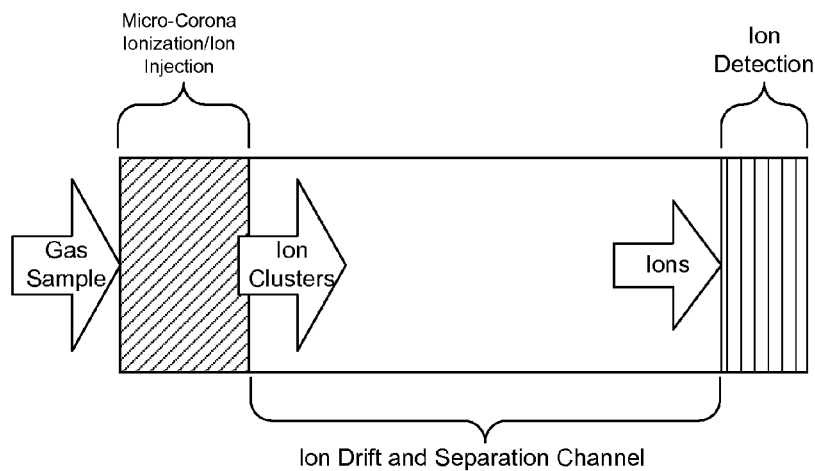
FIG. 1A is a high-level block diagram of an embodiment of an ion separation spectrometer.

FIG. 1A illustrates schematically an embodiment of an ion separation spectrometer (ISS). The ISS includes three main components: a ionization and injection section with an inlet and an outlet, an ion drift and separation channel that has one end coupled to the outlet of the ionization and injection section, and an ion detection section coupled to the ion drift and separation channel at the opposite end from where the ionization and injection section is coupled to the channel. All three elements are aligned substantially along an axis or centerline.

Figure 1B:
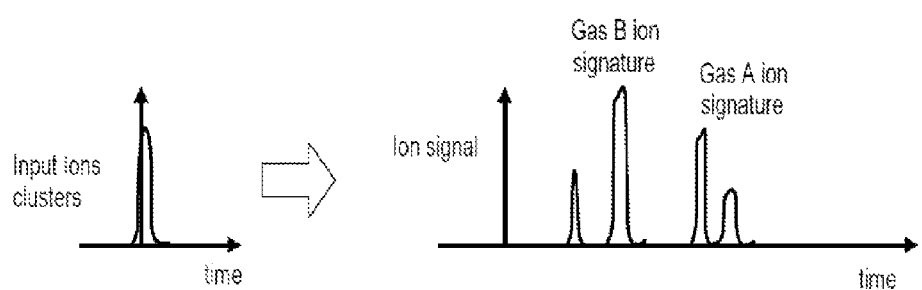
FIG. 1B shows a pair of graphs illustrating results that are possible with the ion separation spectrometer shown in FIG. 1A.

FIGS. 1A and 1B together illustrate the operation of the ISS of FIG. 1A. A gas sample is directed into the ionization and injection section, where chemical atoms or molecules in the gas are ionized and, after ionization, the resulting ion clusters are injected into the drift and separation channel. In the drift and separation channel, the ions are subjected to an electric field. Different ions in the ion clusters will have different charges, different masses, and different cross-sectional shapes and areas. The force exerted on each ion by the electric field will depend on the ion's charge, and the acceleration of each ion in response to the force will depend on it mass. Consequently, subjecting the ion clusters to an electric field has the effect of separating individual ions from the ion clusters and accelerating them at different rates toward the ion detector, such that different ions will reach the detector at different times (i.e., they are separated in the time domain). Since the ions are separated and arrive at the detector at different times, the presence and concentration of the different ions can be sensed based on the time signature of the signal from the ion detector, as shown in FIG. 1B.

Figure 2A:
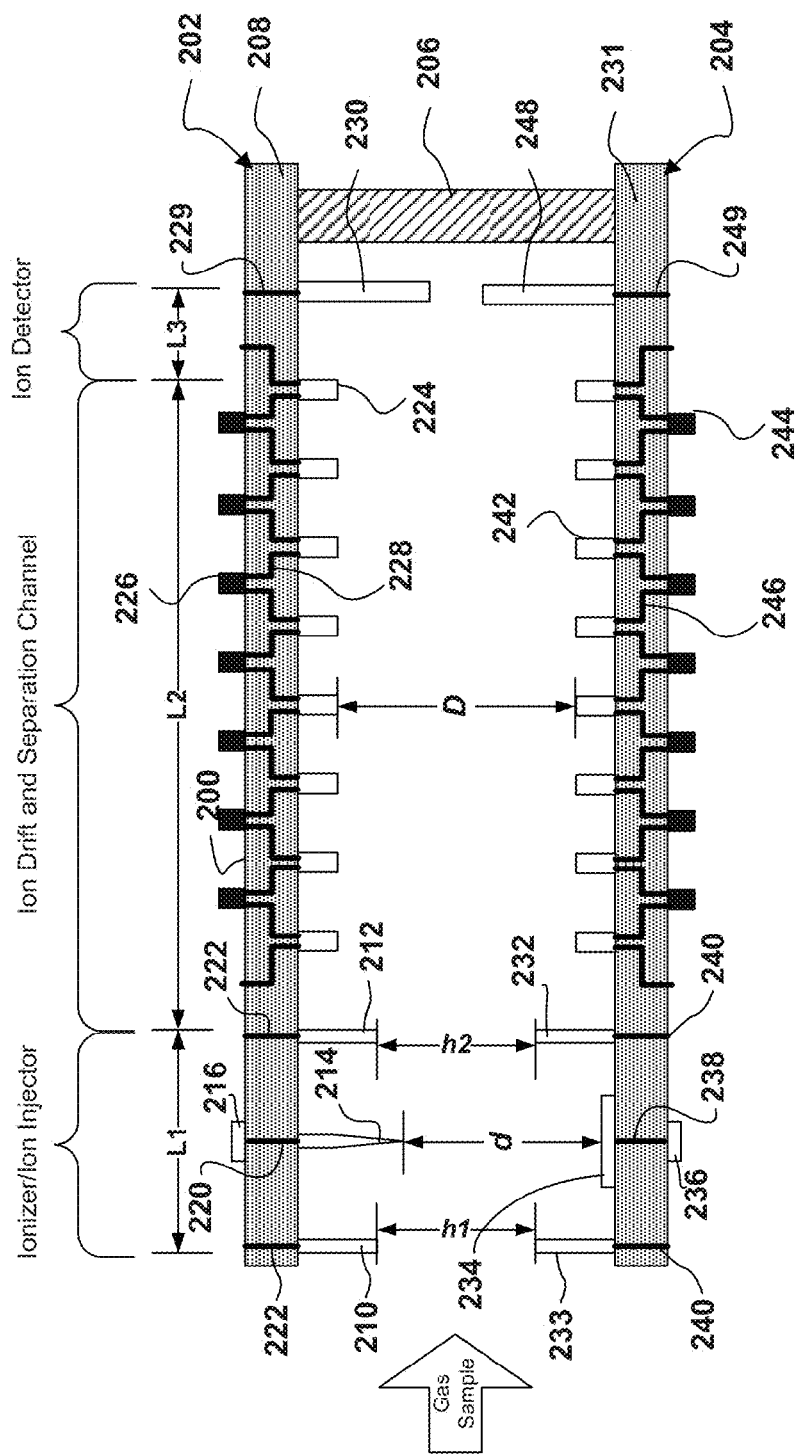
FIG. 2A is a side view of an embodiment of an ion separation spectrometer.

FIG. 2A illustrates an embodiment of an ion separation spectrometer (ISS) 200. The illustrated embodiment is a small-scale micro-ISS that integrates the elements of the ISS into a single chip but, with respect to this or any other embodiment disclosed herein, use of the prefix "micro" does not limit the size of the device or any component thereof, as other larger-scale embodiments of the device and/or its components are also possible.

ISS 200 includes a first subassembly 202 having some elements of the micro-ISS formed on it, a second subassembly 204 having other elements of the micro-ISS formed on it and a spacer 206 between them to keep the sub-assemblies at the desired separation when bonded together as shown. The micro-corona-ISS chip can be fabricated, for example, by micro-electro-mechanical-systems (MEMS) process on a PCB board or silicon wafer for low-cost mass production. Details of subassemblies 202 and 204 are described below in connection with FIGS. 3A-3D. ISS 200 is intended to be operated in ambient pressure but can also be applicable in vacuum environment.

ISS 200 includes four main components: a micro-corona ionizer that ionizes chemical atoms and/or molecules in a gas sample entering the inlet; an ion injector to inject the resulting ions into the drift and separation channel; an ion drift and separation channel; and an ion collector electrode or detector array. The micro-corona ionizer includes a sharp electrode or probe 214 formed on substrate 208 and a planar electrode 234 formed on substrate 231. Probe 214 is electrically coupled to a contact pad 216 on the opposite side of substrate 208 by a conductive path 220. Contact pad 216 and conductive path 220 are used to provide electrical power to probe 214. Similarly, planar electrode 234 is electrically coupled to contact pad 236 on the opposite side of substrate 231 by a conductive path 238. Contact pad 236 and conductive path 238 are used to provide electrical power to planar electrode 234. The sharp probe 214 and the surface of planar electrode 234 are spaced apart by a discharge distance d, which can vary depending, for example, on the voltages to be applied and the chemicals to be ionized in the gas sample. The micro-corona ionizer in the ISS chip is thus used to ionize input gases/VOCs instead of using radioactive material as an ionization source.

The ion injector includes two pairs of injector electrodes. The first pair of injector electrodes is positioned near the inlet of the ion injector and includes electrode 210 formed on substrate 208 and electrode 233 formed on substrate 231. Electrode 210 is separated from electrode 233 by distance h1. Electrode 210 is electrically coupled to a conductive path 222 in or on substrate 208, while electrode 233 is electrically coupled to a conductive path 240 in or on substrate 231. The second pair of injector electrodes is positioned near the outlet of the ion injector and includes electrode 212 formed on substrate 208 and electrode 232 formed on substrate 231. Electrode 212 is separated from electrode 232 by distance h2. Electrode 212 is electrically coupled to a conductive path 222 in or on substrate 208, while electrode 232 is electrically coupled to a conductive path 240 in or on substrate 231. Conductive paths 222 can be used to provide electrical power to electrodes 210 and 212, while conductive paths 240 can be used to provide electrical power to electrodes 231 and 232.

In the illustrated embodiment, the two pairs of injector electrodes are longitudinally spaced apart from each other by distance L1 and the micro-corona ionizer is positioned between the injector electrode pairs. Distance L1 between the pairs of electrodes, as well as the transverse distances h1 and h2 between electrodes, can be determined based on the operational requirements of ISS 200, such as the voltages to be applied and the chemicals to be ionized and injected. In the illustrated embodiment the injector electrodes are all of substantially the same size, but in other embodiments the injector electrodes need not be of the same size: the different injector electrode pairs can have different sized electrodes, the electrodes within each pair can be of different sizes, or both. Moreover, in the illustrated embodiment the injector electrodes are positioned such that the outlet of the ion injector is substantially aligned with a centerline of ISS 200, but in other embodiments the injector electrodes can be sized so that the outlet of the ion injector is off the centerline of ISS 200.

The ion drift and separation channel is coupled to the outlet of the ion injector and includes two sets of separation electrodes: a set of electrodes 224 formed on the side of substrate 208 that defines a wall of the channel, and a set of electrodes 242 formed on the side of substrate 231 that forms another wall of the channel. Separation electrodes 224 and 242 are used to create an electric field in the drift and separation channel to separate ions and accelerate them toward the detector.

Separation electrode sets 224 and 242 are spaced apart from each other by transverse distance D, and the individual electrodes in each set of electrodes are regularly spaced along the substrate in a longitudinal direction. Distance D, as well as the longitudinal spacing between individual electrodes in each set, can be determined based on the operational requirements of ISS 200, such as the ions to be separated, voltages to be applied, length L2 of the channel, and so forth. In the illustrated embodiment, the separation electrode sets 224 and 242 each include eight regularly-spaced electrodes, but in other embodiments each set of electrodes can include any number of electrodes, including a single (i.e., one) electrode, and the longitudinal spacing between individual electrodes in each set need not be regular. Moreover, in the illustrated embodiment both sets of electrodes 224 and 242 have the same number of individual electrodes, but in other embodiments sets of electrodes 224 and 242 need not have the same number of individual electrodes. In still other embodiments, the number of separation electrode sets can be greater or less than the number shown in the illustrated embodiments. Various types of separation electrode configurations and electric field applications can be used in the drift and separation channel to achieve desired ion separation during their travel before reaching the ion detector, as shown in other embodiments described herein.

Individual electrodes within electrode set 224 are electrically coupled by conductive paths 228 to resistors 226 on the opposite side of substrate 208 and, similarly, individual electrodes within electrode set 242 are electrically coupled by conductive paths 246 to resistors 244 on the opposite side of substrate 208. Among other things, resistors 226 and 244 can be used to heat the drift and separation channel. Conductive paths 228 and 246 also provide an electrical coupling between the electrodes and resistors and electrical source so that electrical power can be supplied to the electrodes and resistors. In the illustrated embodiment, the number of individual resistors matches the number of electrodes, but in other embodiments that need not be the case.

The ion detector is positioned at the end of the drift and separation channel opposite the end where the channel is coupled to the ion injector. The ion detector has a longitudinal dimension L3, corresponding roughly to the distance between the last individual separation electrode and the sensor or detector. In the illustrated embodiment, the sensor includes sensor electrode (also referred to as a "sense electrode") 230 formed on substrate 208 and a sensor electrode 248 formed on substrate 231. Sensor electrode 230 is electrically coupled to a conductive path 229 that leads to the side of substrate 208 opposite the side where electrode 230 is formed, while sensor 248 is electrically coupled to a conductive path 249 that leads to the side of substrate 231 opposite the side where electrode 248 is formed. Conductive paths 229 and 249 provide a way for circuits and associated logic to be coupled to electrodes 230 and 248 to read, condition and process signals generated by electrically charged ions received at the sensor electrodes. The presence and/or concentration of specific gases or chemicals can be determined based on the spectrum signature of the signals from the sensor electrodes. In the illustrated embodiment two sensor electrodes of similar size are shown at the same longitudinal position, but other embodiments can include a lesser or greater number of electrodes and in other embodiments the electrodes need not be at the same longitudinal position and need not have the same size.

Figure 2B:
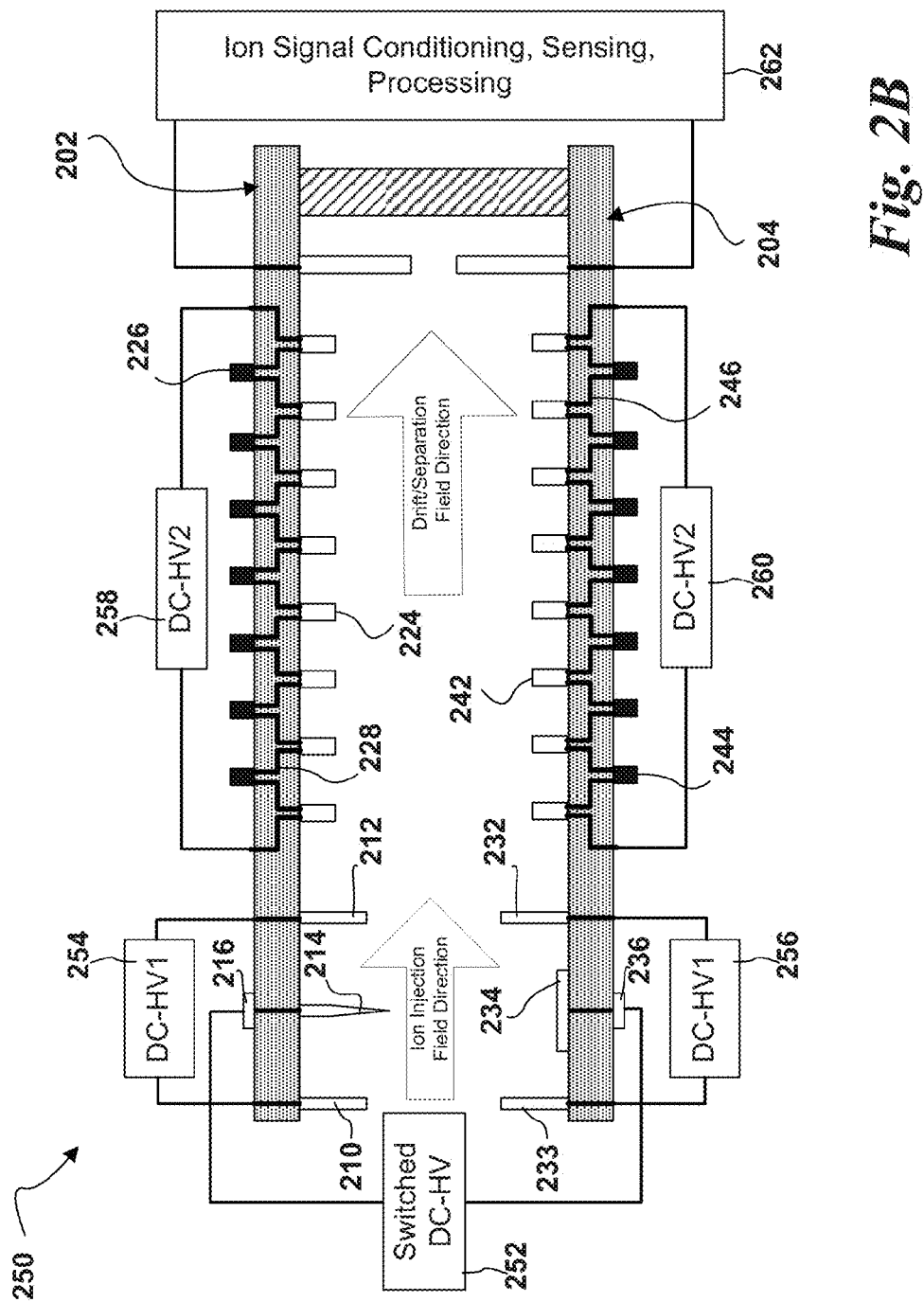
FIG. 2B is a side view of the embodiment of the ion separation spectrometer shown in FIG. 2A, illustrating an embodiment of electrical connections that can be used with the spectrometer.

FIG. 2B illustrates an embodiment of the electrical connections that can be used for ISS 200. A switched direct-current (DC) high voltage (DC-HV) source 252 is electrically connected to probe 214 through contact pad 216 and conductive path 220, and is also electrically connected to planar electrode 234 through contact pad 236 and conductive path 238. Switched DC-HV source 252 can apply high voltages between probe 214 and planar electrode 234 to ionize chemicals in a gas sample injected into ISS 200. The exact voltage applied by DC-HV source 252 can depend on factors such as the separation distance d and the chemicals to be ionized, while the duration of the switched high voltage can vary from nanoseconds to greater than milliseconds depending on the operational requirements. In one embodiment, DC-HV source 252 can apply voltages between 0V and 1000V, but in other embodiments it can apply voltages outside this range.

The injector electrodes are similarly connected to separate DC high voltage (DC-HV1) sources. Injector electrodes 210 and 212 are coupled to DC-HV1 source 254 through conductive paths 222, while injector electrodes 231 and 232 are coupled to DC-HV1 source 256 through conductive paths 240. The voltages applied by DC-HV1 source 254 and DC-HV1 source 256 will determine the initial ion injection velocity into the drift and separation channel. In one embodiment, DC-HV1 sources 254 and 256 can apply voltages between 0V and 1000V, but in other embodiments they can apply voltages outside this range.

Electrode sets 224 and 242 are electrically coupled to the same or separate DC high-voltage (DC-HV2) sources. Electrode set 224 is coupled to DC-HV2 source 258 through conductive paths 228, while electrode set 242 is coupled to DC-HV2 source 260 through conductive paths 246. With electrode sets 224 and 242 uniformly spaced apart by distance D, and individual electrodes regularly spaced within each set, the voltages applied by DC-HV2 source 258 and 260 produce a uniform longitudinal electric field along the ion travel direction. The HV2 voltage will determine the ion drift time before reaching the detector. In one embodiment, DC-HV2 sources 258 and 260 can apply voltages between 500V and 1000V, but in other embodiments they can apply voltages outside this range.

Detector electrodes 230 and 248 are electrically coupled to circuitry and logic 262 to read, condition and/or process signals received from the detector electrodes for quantitative gas ion analysis. Detector electrode 230 is coupled to circuitry and logic 262 through conductive paths 229, while detector electrode 248 is coupled to circuitry and logic 262 through conductive paths 249.

Figure 2C:
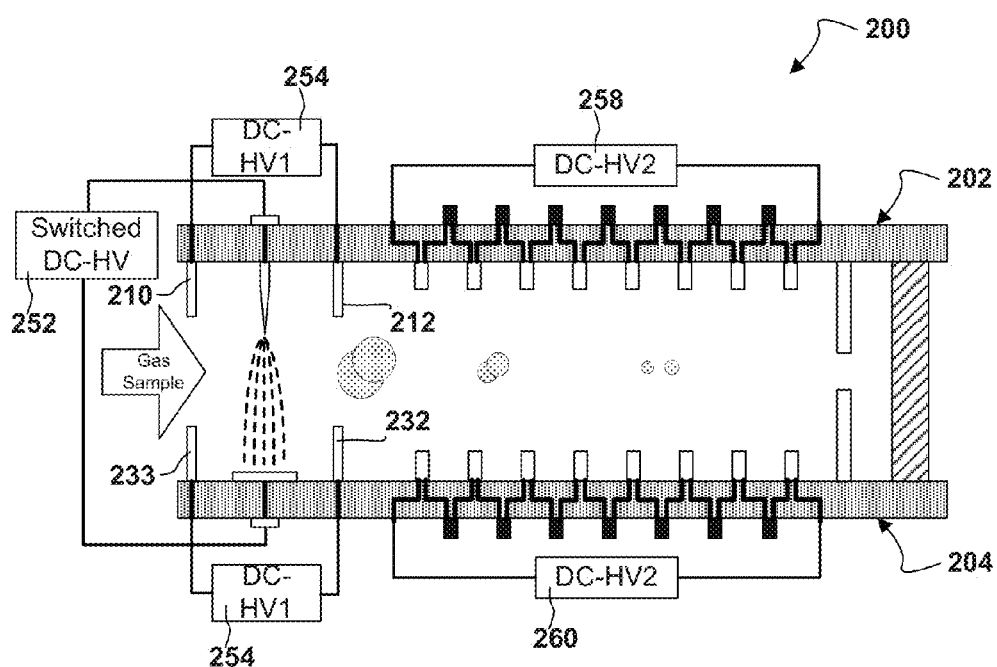
FIG. 2C is a diagram illustrating an embodiment of the operation of the ion separation spectrometer shown in FIG. 2B.
Figure 7:
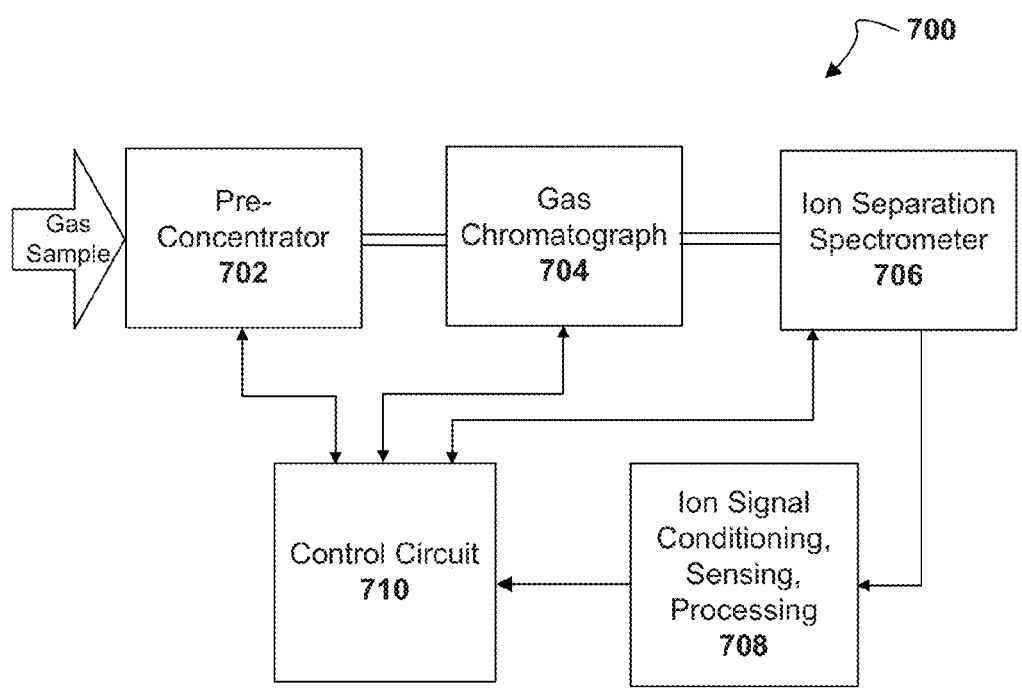
FIG. 7 is a schematic drawing of an embodiment of a gas analysis system using an embodiment of an ion separation spectrometer.

FIG. 2C diagrammatically illustrates the operation of an embodiment of ISS 200 having the electrical connections shown in FIG. 2B. When gas analytes are introduced to ISS 200, for example by a gas chromatograph as shown in FIG. 7, the micro-corona ionizer is pulse-switched, which ionizes the input gases/chemicals. If not already resolved (separated) by another component such as a gas chromatograph, the micro-corona ionizer simultaneously creates ion clusters from different gases/chemicals. The ion clusters are then swept into the ion drift and separation channel by the ion injector (if an injection voltage is applied, DC-HV1≠0) or by gas flow (if no injection voltage is applied, DC-HV1=0). Different ions have different mass and corresponding cross-section resistance when traveling through the ambient within the drift and separation channel. The ion clusters are then separated in time and sensed by the ion detector/electrode due to different traveling velocities along the drift and separation channel. By evaluating the ion current signal pattern received from the sensor electrodes, specific gases/chemicals that are not separated by other devices such as a gas chromatograph can be further distinguished by ISS 200. The ion signal strength determines the corresponding input chemical concentration.

Figure 3A:
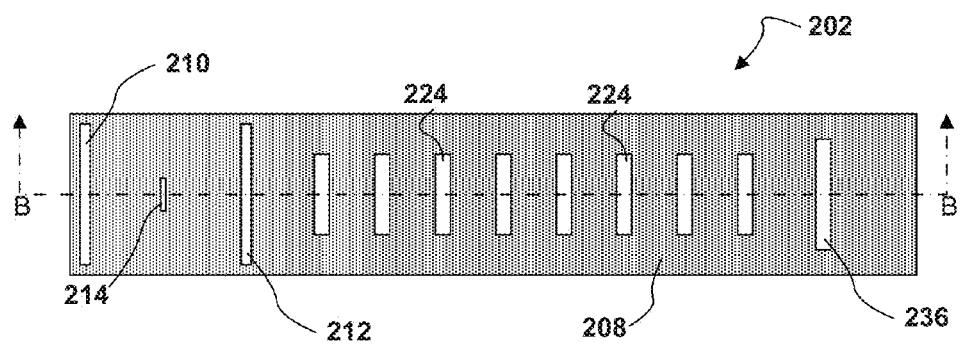
FIGS. 3A-3D are diagrams illustrating an embodiment of the construction of the ion separation spectrometer shown in FIG. 1A.
Figure 3B:
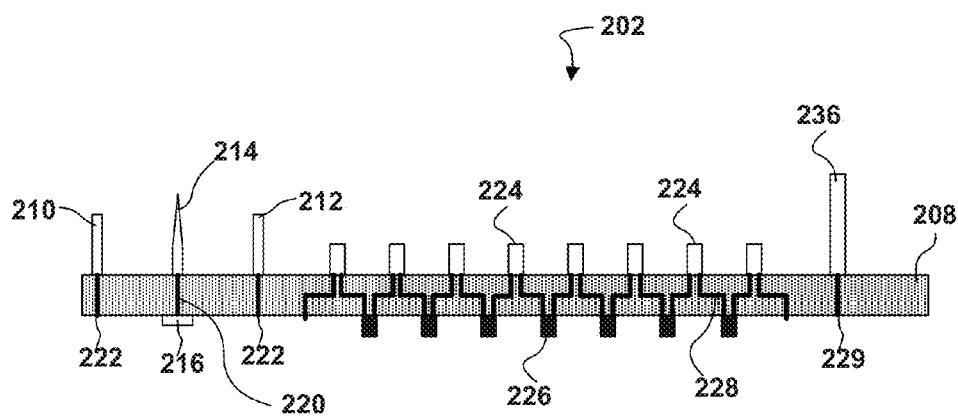

FIGS. 3A-3D illustrate an embodiment of the construction of first subassembly 202 and second subassembly 204, which are bonded together with spacer 206 to form ISS 200 (see FIG. 2A). FIGS. 3A-3B together illustrate an embodiment of the construction of first subassembly 202. Subassembly 202 includes a substrate 208 having several components formed thereon. Probe 214, injector electrodes 210 and 212, electrode set 224 and detector electrode 236 are formed on one side of substrate 208, while resistor set 226 and contact pad 216 are formed on the other side of substrate 208. In one embodiment all the electrodes can be metal and can be fabricated to desired sizes by electro-plating or direct printing, but in other embodiments semiconductors or other non-metal conductors can be used for electrodes. In other embodiments, different fabrication approaches are also possible. For example, where ISS 200, and hence subassembly 202, is to be a small-scale device, such as a MEMS-scale device, processes such as photolithographic patterning and etching can be used (see, e.g., FIGS. 4A-4C).

Substrate 208 can be any kind of substrate that can support the components formed on it and that can withstand the manufacturing and operating conditions that will be faced. In one embodiment, substrate 208 can be a single-layer or multi-layer printed circuit board (PCB), but in other embodiments substrate 208 can be another type of substrate such as wafers of silicon, single crystal silicon, silicon-on-insulator (see FIG. 4C), glass, ceramic, or low temperature co-fired ceramic (LTCC) technology.

In subassembly 202, conductive path 220 extends from contact pad 216 to probe 214 to provide electrical power to the probe. Similarly, conductive paths 222 extend through substrate 208 to provide electrical connection for injector electrodes 210 and 212, and conductive path 228 extends through substrate 208 to provide electrical connection between electrode set 224 and resistor set 226, as well as to provide a path through which electrical power can be supplied to electrode set 224 and resistor set 226. Finally, conductive path 229 can be used to provide an electrical connection between detector electrode 236 and circuitry and logic that can be used to detect the signal generated by ions arriving at the detector electrode. In the illustrated embodiment, the conductive paths can be a combination of metal traces and vias within the substrate, such as those which can be found in a multi-layer printed circuit board or those which can be patterned, deposited and etched into a substrate using photolithographic techniques. In other embodiments, the conductive paths can instead be printed or patterned and etched on the surfaces of the substrate instead of going through the interior of the substrate. In still other embodiments, the conductive paths can be separate components such as wires.

Figure 3C:
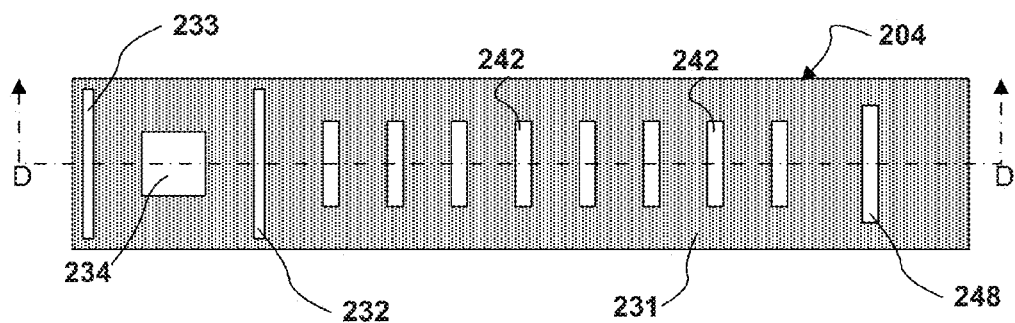
Figure 3D:
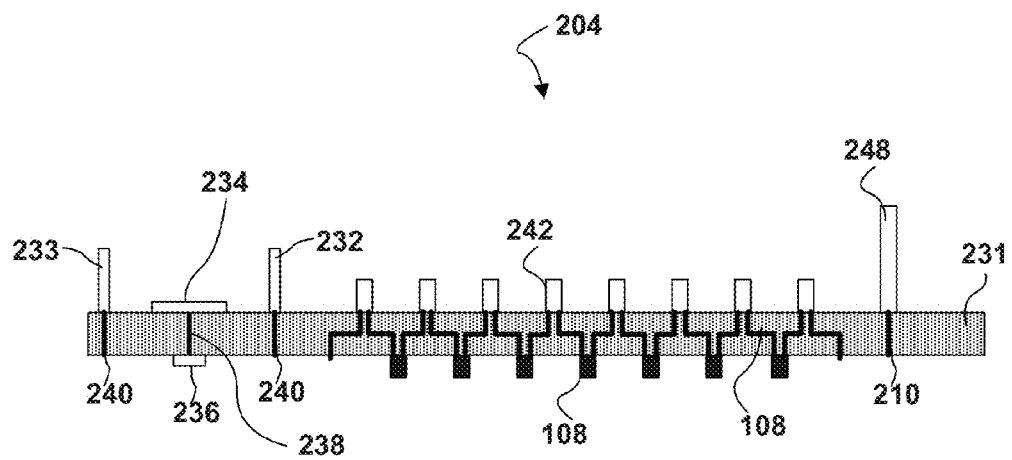

FIGS. 3C-3D together illustrate an embodiment of the construction of second subassembly 204. Subassembly 204 includes a substrate 231 having several components formed thereon. Planar electrode 234, injector electrodes 232 and 233, electrode set 242 and detector electrode 248 are formed on one side of substrate 231, while resistor set 226 and contact pad 236 are formed on the other side of substrate 208. The principal difference between subassembly 204 and subassembly 202 is the presence in subassembly 204 of planar electrode 234 instead of probe 214. Subassembly 204 can be manufactured using any technique that can be used to manufacture subassembly 202, and the variations applicable to subassembly 202 and its components are equally applicable to subassembly 204 and its components.

Figure 4A:
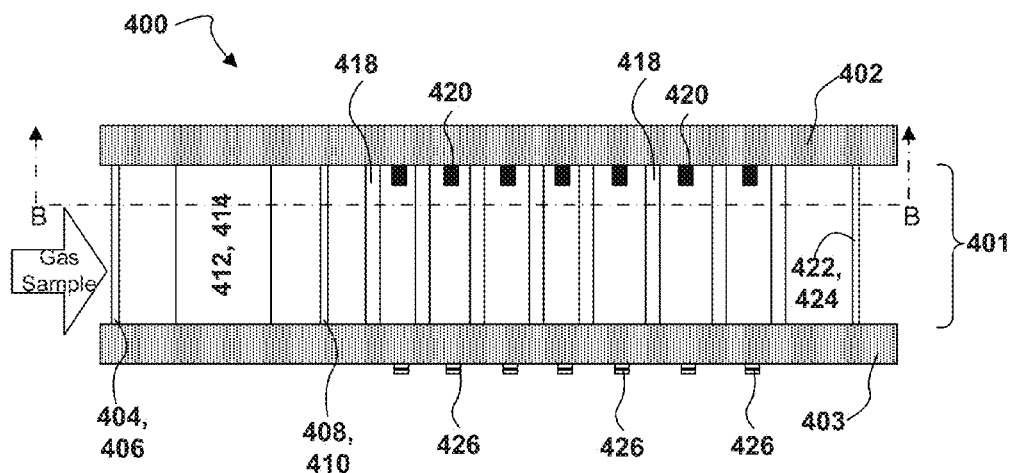
FIGS. 4A-4B are a side view and a plan view, respectively, of an alternative embodiment of an ion separation spectrometer.
Figure 4B:
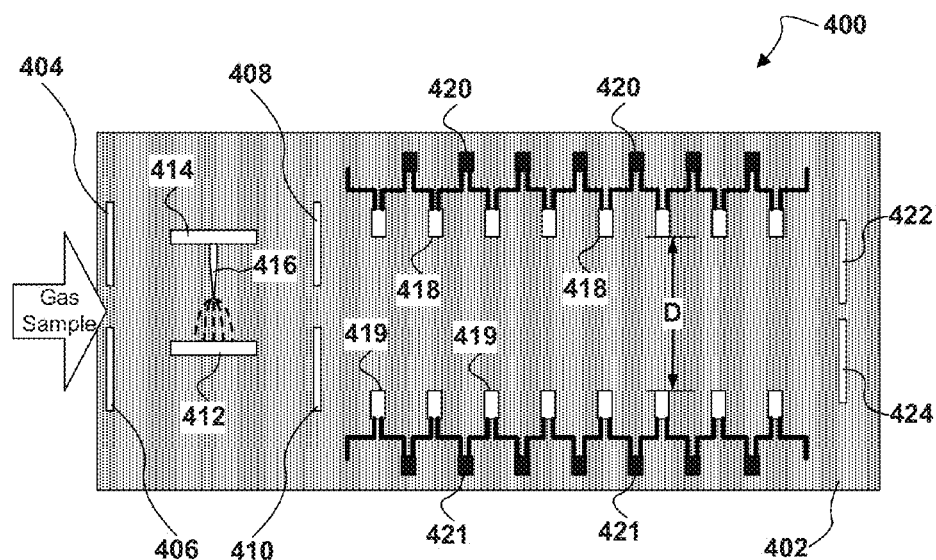

FIGS. 4A-4B together illustrate an alternative embodiment of a MEMS-scale micro-ISS 400. Like ISS 200, micro-ISS 400 is intended to be operated in ambient pressure but can also be used in a vacuum environment. Micro-ISS 400 is fabricated on a silicon wafer 401 sandwiched by a first glass wafer 402 and a second glass wafer 403. Most of the elements of detector 400 are formed in silicon wafer 401 using processes such as lithographic patterning and etching. Injector electrodes 404, 406, 408 and 410 are formed in silicon wafer 401. The micro-corona ionizer is also formed in silicon wafer 401 between the pair of injector electrodes 404 and 406 and the other pair of injector electrodes 408 and 410. In the illustrated embodiment, the micro-corona ionizer includes planar electrodes 412 and 414. Sharp-tipped (i.e., sharp knife-edged) probe 416 projects from planar electrode 414 toward planar electrode 412. As in detector 200, the distance between the sharp knife-edge of probe 416 and planar electrode 412 will depend on such factors as the chemicals to be ionized, the voltage to be applied, and so on. The probe and discharge gap is formed directly by lithographically etching the silicon with optical mask. The gap can be precisely defined by the optical mask design in such case. All the separation electrodes can also be simultaneously constructed in the same process.

Electrode sets 418 and 419 are also formed in silicon wafer 401, as are detector electrodes 422 and 424. Resistors 420 can be formed on glass wafer 403 before bonding to the silicon and electrically coupled to the individual separation electrodes within electrode set 418, while resistors 421 can also be formed on glass wafer 403 and electrically coupled to individual separation electrodes 419. A heater including one or more heating elements 426 can be formed on glass wafer 403, on the side of the wafer opposite where the wafer is joined to silicon wafer 401. Although not shown in the figure, conductive paths can be provided in or on silicon wafer 401, glass wafer 402 and/or glass wafer 403 to provide the necessary electrical connections for the different components. Although micro-ISS 400 is of a different construction than ISS 200, all its elements are subject to the same variations in size, positioning, number, construction, and so on described above for the elements of ISS 200.

Figure 4C:
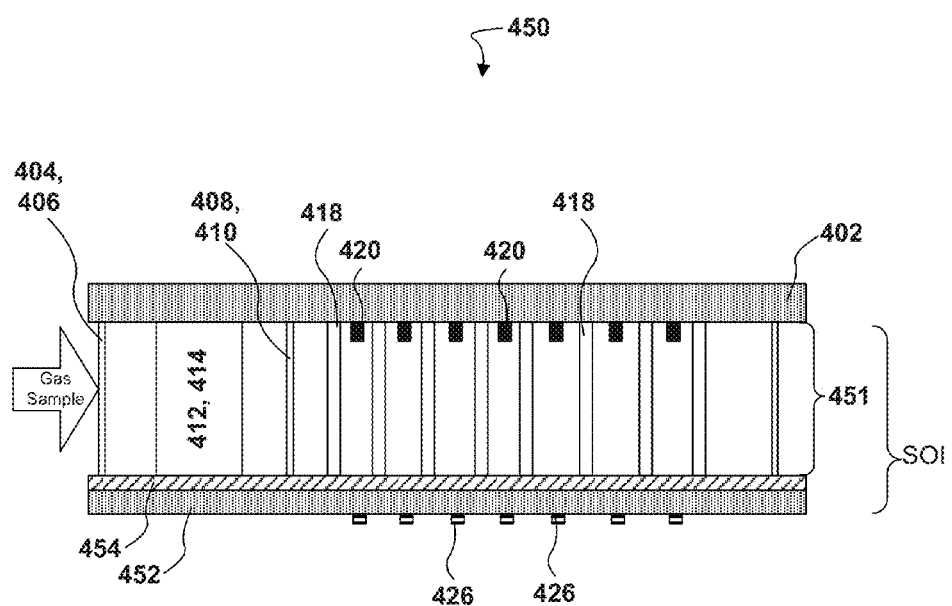
FIG. 4C is a side view of an alternative embodiment of the ion separation spectrometer shown in FIGS. 4A-4B.

FIG. 4C illustrates an alternative embodiment of a micro-ISS 450. Micro-ISS 450 is in most respects similar to micro-ISS 400. The primary difference is that in micro-ISS 450 most of the components are formed in a silicon layer 451 that forms part of a thick silicon-on-insulator (SOI) wafer that includes a base layer 452, an insulator layer 454, and silicon layer 451. In other words, micro-ISS 450 replaces the glass wafer 403 and silicon wafer 401 of micro-ISS 400 with an SOI wafer. Glass wafer 402 is used in the same position and for the same function as it is in micro-ISS 400. The same manufacturing techniques used for micro-ISS 400 can be used for micro-ISS 450.

Figure 5A:
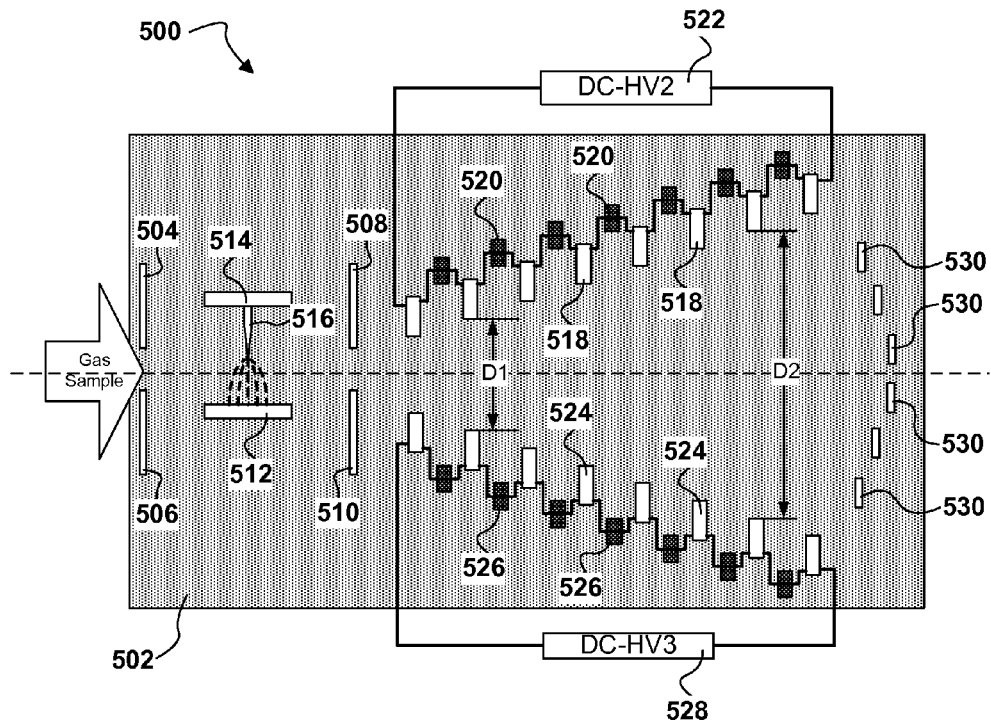
FIG. 5A is a plan view of an alternative embodiment of an ion separation spectrometer.

FIG. 5A illustrates an alternative embodiment of a micro-ISS 500. Like ISS 400, micro-ISS 500 is intended to be operated in ambient pressure but can also be used in a vacuum environment. In the illustrated embodiment, micro-ISS 500 is a MEMS ISS that can be manufactured in a silicon wafer sandwiched between two substrates such as glass plates, as shown in FIGS. 4A and 4B, or can be manufactured in a SOI wafer as shown in FIG. 4C. In other embodiments, ISS 500 can be manufactured differently and need not be a MEMS or MEMS-scale device. Additionally, all elements of micro-ISS 500 are subject to the same variations in size, positioning, number, construction, and so on described above for the elements of detector 200.

Micro ISS 500 includes injector electrodes 504, 506, 508 and 510. Also formed between the injector electrodes is the micro-corona ionizer. In the illustrated embodiment, the micro-corona ionizer includes planar electrodes 512 and 514. Sharp-tipped probe 516 projects from planar electrode 514 toward planar electrode 412. As in the other described embodiments, the discharge distance between the tip of probe 516 and planar electrode 512 will depend on such factors as the chemicals to be ionized, the voltage to be applied, and so on.

Separation electrode sets 518 and 524 are also formed in silicon wafer 401, and resistors 520 can be electrically coupled to the individual separation electrodes within separation electrode set 518, while resistors 526 can be electrically coupled to individual separation electrodes in separation electrode set 524. In micro-ISS 500, separation electrode sets 518 and 524 are not spaced apart by a uniform distance D as in ISS 400, but instead the spacing between the separation electrode sets varies in the longitudinal dimension. In the illustrated embodiment, the spacing increases (i.e., it diverges) linearly with longitudinal distance from the injector, such that the spacing at a first longitudinal position is D1, while the spacing at a second longitudinal position further from the injector is D2, with D2 being greater than D1. In other embodiments, the spacing between separation electrode sets need not vary linearly with longitudinal position, and in still other embodiments the spacing need not increase with longitudinal positions but can instead decrease (converge) with longitudinal position. In still other embodiments, the variation of spacing with longitudinal position need not be monotonic as shown.

Figure 5B:
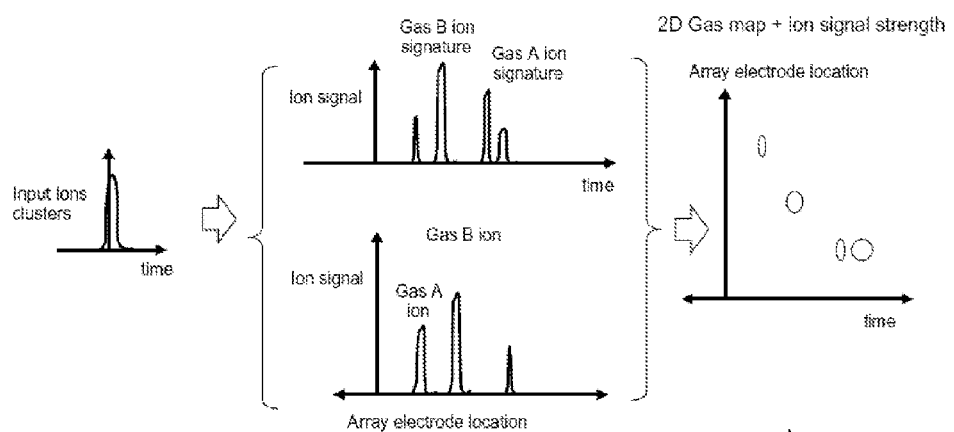
FIG. 5B shows a pair of graphs illustrating results that are possible with the ion separation spectrometer shown in FIG. 5A.

In micro-ISS 500, separation electrode set 518 is coupled to a direct current high voltage (DC-HV2) source 522, while separation electrode set 524 is coupled to another direct current high voltage (DC-HV3) source 528. Two or more different DC high voltages (DC-HV2 and DC-HV3) can be applied to the separation electrodes to create both longitudinal and transverse electric fields along the ion travel direction. In such case, different ions will travel with different curvatures and velocities towards the sensor electrodes 530. An array of sense electrodes 530 are positioned at multiple designed to detect different-curvature ions separately, as shown in FIG. 5B.

In micro-ISS 500, an array of detector electrodes 530 is formed at the end of the drift and separation channel opposite the ion injector. In the illustrated embodiment, six detectors 530 are symmetrically positioned about a centerline and are positioned at several different longitudinal positions. In other embodiments, the number of detectors can vary, the detectors need not be symmetrically positioned about the centerline, and need not be positioned at different longitudinal positions. In an embodiment where longitudinal and transverse electric fields are created by applying different voltages to the sets of separation electrodes, the detector array provides an additional gas ion spatial distribution, resulting in a powerful two-dimensional gas/chemical spectrum pattern mapping that separates ions in both time and space, as shown in FIG. 5B. Therefore, it can drastically improve the selectivity of micro-ISS 500.

A heater including one or more heating elements (not shown) can be formed micro-ISS 500, on the side of the wafer opposite where the wafer is joined to silicon wafer 401. As with ISSs 400 and 450, conductive paths (also not shown) can be provided in or on the wafers that form micro-ISS 500 to provide the necessary electrical connections for the different components.

Figure 6:
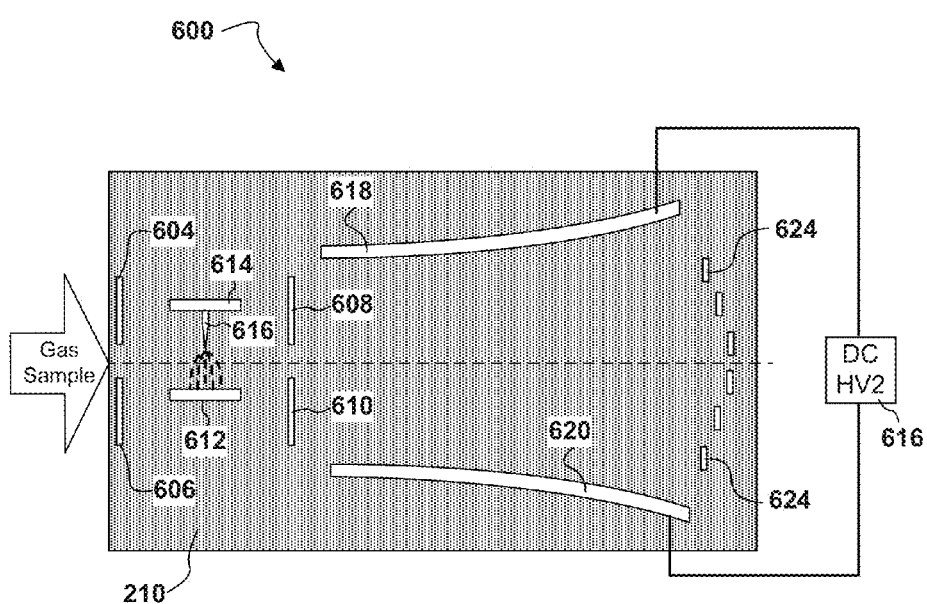
FIG. 6 is a plan view of another alternative embodiment of an ion separation spectrometer.

FIG. 6 illustrates an alternative embodiment of a micro-corona-ISS 600 with separation electrodes and a sensor electrode array for 2D spectrum pattern mapping. Like the other ISS embodiments described herein, micro-ISS 600 is intended to be operated in ambient pressure but can also be used in a vacuum environment. Micro-ISS 600 is in most respects similar to micro-ISS 500. The primary difference is that simple curved separation electrodes 618 and 620 can be designed on each side of the drift and separation channel. A DC high voltage (HV2) is directly applied between the two electrodes, producing a transverse electric field across the injected ions from the micro-corona ionizer and the injector. Similar to configuration in FIG. 5A, gas ions with different traveling curvatures are detected by separate electrodes, and thus, 2D spectrum pattern mapping can be obtained as shown, for example, in FIG. 5B.

FIG. 7 illustrates an embodiment of a gas detection system 700 in which embodiments of an ISS, such as those described above, can be used. System 700 includes a pre-concentrator 702 coupled by a fluid connection to a gas chromatograph 704. Gas chromatograph 704 is in turn coupled by a fluid connection to ion separation spectrometer (ISS) 706, which can, in some embodiments, be any of the ISS embodiments described above. ISS 706 is coupled to ion sensing, conditioning and processing circuitry and logic 708. A control circuit and associated logic 710 is coupled to circuitry and logic 708, as well as to pre-concentrator 702, gas chromatograph 704 and ISS 706.

Pre-concentrator 702 includes an inlet through which a gas sample enters an outlet coupled to gas chromatograph 704. As the gas sample flows through pre-concentrator 702, the pre-concentrator absorbs certain chemicals from the gas sample, thus concentrating those chemicals for later separation and detection. In one embodiment of system 700 pre-concentrator 702 can be a MEMS pre-concentrator, but in other embodiments pre-concentrator 702 can be a non-MEMS chip scale device.

Gas chromatograph 704 includes an inlet coupled to pre-concentrator 702 and an outlet coupled to ISS 706. Gas chromatograph 704 receives fluid from pre-concentrator 702 and outputs fluid to ISS 706. As fluid received from pre-concentrator 702 flows through gas chromatograph 704, individual chemicals in the gas sample received from the pre-concentrator are separated from each other in the time domain for later input into ISS 706. In one embodiment of system 700 gas chromatograph 704 can be a MEMS gas chromatograph, but in other embodiments gas chromatograph 108 can be a non-MEMS chip scale device.

ISS 706 is coupled to gas chromatograph 704. As fluid flows into ISS 706, the chemicals that were not separated by gas chromatograph 704 enter the ISS and their presence and/or concentration is sensed by sensors within the ISS, as described above. ISS 706 achieves ionized gases/chemical separation and sensing, for chemicals which are not separated by the micro-GC chip. As a result, it provides the 2nd stage gases/VOCs separation, which further improves the system's selectivity between similar gas or chemical analytes. When ISS 706 is configured and integrated with pre-concentrator 702 and gas chromatograph 704 in the same system as shown in FIG. 7, it can reach gas/chemical limit of detection (LOD) in range of parts-per-billion (ppb) to part-per-trillion (ppt).

Sensing, conditioning and processing circuit 708 is coupled to an output of ISS 706 such that it can receive data signals from individual sensors within ISS 706 and process and analyze these data signals. In one embodiment, circuit 708 can be an application-specific integrated circuit (ASIC) designed specifically for the task, such as a CMOS controller including processing, volatile and/or non-volatile storage, memory and communication circuits, as well as associated logic to control the various circuits and communicate externally. In other embodiments, however, circuit 708 can instead be a general-purpose microprocessor in which the control functions are implemented in software. Although shown in the figure as having all three functions—sensing, conditioning and processing—in other embodiments these functions need not all be present, or can be present in different circuits. Circuit 708 is also coupled to control circuit 710 and can send signals to, and receive signals from, control circuit 710 so that the two circuits can coordinate and optimize operation of system 700. Although the illustrated embodiment shows control circuit 710 and circuit 708 as physically separate units, in other embodiments the controller and the readout and analysis circuit could be combined in a single unit.

Control circuit 710 is communicatively coupled to the individual elements within system 700 such that it can send control signals and/or receive feedback signals from the individual elements. In one embodiment, control circuit 710 can be an application-specific integrated circuit (ASIC) designed specifically for the task, for example a CMOS controller including processing, volatile and/or non-volatile storage, memory and communication circuits, as well as associated logic to control the various circuits and communicate externally to the elements of system 700. In other embodiments, however, control circuit 710 can instead be a general-purpose microprocessor in which the control functions are implemented in software.

The above description of illustrated embodiments of the invention, including what is described in the abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above detailed description.

The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

The invention claimed is:

1. An apparatus comprising:
an ion injector having an inlet and an outlet;
a micro-corona ionizer positioned between the inlet and the outlet of the ion injector;
a drift and separation channel having a first end and a second end, the first end being coupled to outlet of the ion injector, the drift and separation channel including:
a first channel wall having a first set of separation electrodes thereon comprising a plurality of electrically coupled individual separation electrodes with resistors electrically coupled between one or more pairs of individual electrodes, the first set of separation electrodes being coupled to a first direct current (DC) voltage source, and
a second channel wall having a second set of separation electrodes thereon comprising a plurality of electrically coupled individual separation electrodes with resistors electrically coupled between one or more pairs of individual electrodes, the second set of separation electrodes being spaced apart from the first set of separation electrodes and coupled to a second DC voltage source, wherein the first and second DC voltage sources are the only voltage sources coupled to the separation electrodes; and
an ion detector coupled to the second end of the ion separation and drift channel.

2. The apparatus of claim 1 wherein the micro-corona ionizer comprises:
a planar electrode; and
a sharp knife-edged electrode spaced apart from the planar electrode and positioned with the sharp tip pointing toward the planar electrode.

3. The apparatus of claim 2, further comprising a voltage source coupled to the planar electrode and the sharp knife-edged electrode.

4. The apparatus of claim 1 wherein the ion injector comprises:
a first pair of injection electrodes; and
a second pair of injection electrodes spaced apart from the first pair of injection electrodes.

5. The apparatus of claim 4 wherein the micro-corona ionizer is positioned between the first pair of injection electrodes and the second pair of injection electrodes.

6. The apparatus of claim 4, further comprising a voltage source coupled between the first pair of injection electrodes and the second pair of injection electrodes.

7. The apparatus of claim 1 wherein the voltage applied to the first set of separation electrodes is different than the voltage applied to the second set of separation electrodes.

8. The apparatus of claim 1 wherein the spacing between the first set of separation electrodes and the second set of separation electrodes is constant.

9. The apparatus of claim 1 wherein the spacing between the first set of separation electrodes and the second set of separation electrodes varies from the first end of the channel to the second end of the channel.

10. The apparatus of claim 1 wherein the ion detector comprises an array of at least two sensor electrodes positioned about a centerline of the drift and separation channel.

11. The apparatus of claim 10, further comprising a reading circuit and logic coupled to the array of sensor electrodes to sense and read signals generated by each sensor electrode.

12. The apparatus of claim 11, further comprising a conditioning circuit and logic coupled to the reading circuitry to condition signals received from the reading circuit.

13. The apparatus of claim 1 wherein the resistors in each set of separation electrodes are positioned on an outside wall of the drift and separation channel.

14. The apparatus of claim 1 wherein the resistors in each set of separation electrodes are connected in series between the one or more pairs of individual electrodes.

15. A process comprising:
ionizing chemicals in a gas sample using a micro-corona ionizer;
injecting the ionized chemicals into a drift and separation channel, the drift and separation channel including:
a first channel wall having a first set of separation electrodes thereon comprising a plurality of electrically coupled individual separation electrodes with resistors electrically coupled between one or more pairs of individual electrodes, the first set of separation electrodes being coupled to a first direct current (DC) voltage source, and
a second channel wall having a second set of separation electrodes thereon comprising a plurality of electrically coupled individual separation electrodes with resistors electrically coupled between one or more pairs of individual electrodes, the second set of separation electrodes being spaced apart from the first set of separation electrodes and coupled to a second DC voltage source, wherein the first and second DC voltage sources are the only voltage sources coupled to the separation electrodes;
time-domain separating the chemical ions from each other in the drift and separation channel; and
detecting the time-domain separated chemical ions.

16. The process of claim 15 wherein ionizing chemicals in the gas sample using the micro-corona ionizer comprises:

directing the gas sample into a space between a planar electrode and a sharp knife-edged electrode spaced apart from the planar electrode, wherein the sharp knife-edged electrode is positioned with the sharp tip pointing toward the planar electrode; and applying a voltage between the planar electrode and the sharp knife-edged electrode.

17. The process of claim 15 wherein injecting the ionized chemicals comprises:

positioning the ionized chemicals between a first pair of injection electrodes and a second pair of injection electrodes spaced apart from the first pair of injection electrodes; and applying a voltage between the first pair of injection electrodes and the second pair of injection electrodes.

18. The process of claim 15 wherein time-domain separating the chemical ions from each other comprises:

injecting the chemical ions into a drift and separation channel between a first set of separation electrodes and a second set of separation electrodes spaced apart from the first set of separation electrodes; and applying a direct current (DC) voltage to the first set of separation electrodes and to the second set of separation electrodes.

19. The apparatus of claim 18 wherein the voltage applied to the first set of separation electrodes is different than the voltage applied to the second set of separation electrodes.

20. The process of claim 15 wherein detecting the time-domain separated chemical ions comprises:

receiving the time-domain separated chemical ions at an array of at least two sensor electrodes; and generating a signal in each electrode indicative of the ions received at that electrode.

21. The process of claim 20, further comprising reading the signals generated by the sensor electrodes.

22. The process of claim 21, further comprising conditioning signals read from the sensor electrodes.

23. The process of claim 15 wherein the resistors in each set of separation electrodes are positioned on an outside wall of the drift and separation channel.

24. The process of claim 15 wherein the resistors in each set of separation electrodes are connected in series between the one or more pairs of individual electrodes.

25. A system comprising:

a gas chromatograph having an inlet and an outlet;

a detector coupled to the outlet of the gas chromatograph, the detector comprising:

an ion injector having an inlet and an outlet, wherein the inlet of the ion injector is coupled to the outlet of the gas chromatograph;

a micro-corona ionizer positioned between the inlet and the outlet of the ion injector;

an ion separation and drift channel having a first end and a second end, the first end being coupled to outlet of the ion injector, the drift and separation channel including:

a first channel wall having a first set of separation electrodes thereon comprising a plurality of electrically coupled individual separation electrodes with resistors electrically coupled between one or more pairs of individual electrodes, the first set of separation electrodes being coupled to a first direct current (DC) voltage source, and a second channel wall having a second set of separation electrodes thereon comprising a plurality of electrically coupled individual separation electrodes with resistors electrically coupled between one or more pairs of individual electrodes, the second set of separation electrodes being spaced apart from the first set of separation electrodes and coupled to a second DC voltage source, wherein the first and second DC voltage sources are the only voltage sources coupled to the separation electrodes; and an ion detector coupled to the second end of the ion separation and drift channel.

26. The system of claim 25 wherein the micro-corona ionizer comprises:

a planar electrode; and a sharp knife-edged electrode spaced apart from the planar electrode and positioned with the sharp tip pointing toward the planar electrode.

27. The system of claim 26, further comprising a voltage source coupled to the planar electrode and the sharp knife-edged electrode.

28. The system of claim 25 wherein the ion injector comprises:

a first pair of injection electrodes; and a second pair of injection electrodes spaced apart from the first pair of injection electrodes.

29. The system of claim 28 wherein the micro-corona ionizer is positioned between the first pair of injection electrodes and the second pair of injection electrodes.

30. The system of claim 28, further comprising a voltage source coupled between the first pair of injection electrodes and the second pair of injection electrodes.

31. The system of claim 25 wherein the voltage applied to the first set of separation electrodes is different than the voltage applied to the second set of separation electrodes.

32. The system of claim 25 wherein the spacing between the first set of separation electrodes and the second set of separation electrodes is constant.

33. The system of claim 25 wherein the spacing between the first set of separation electrodes and the second set of separation electrodes varies from the first end of the channel to the second end of the channel.

34. The system of claim 25 wherein the ion detector comprises an array of at least two sensor electrodes positioned about a centerline of the drift and separation channel.

35. The system of claim 34, further comprising a reading circuit and logic coupled to the array of sensor electrodes to sense and read signals generated by each sensor electrode.

36. The system of claim 34, further comprising a conditioning circuit and logic coupled to the reading circuit to condition signals received from the reading circuit.

37. The system of claim 36, further comprising a processing circuit and logic coupled to the conditioning circuitry to process the conditioned signals.

38. The system of claim 37, further comprising a control circuit and logic coupled to the ion sensor, the gas chromatograph, and the processing circuit.

39. The system of claim 25, further comprising a preconcentrator coupled to the inlet of the gas chromatograph.

40. The system of claim 25 wherein the resistors in each set of separation electrodes are positioned on an outside wall of the drift and separation channel.

41. The system of claim 25 wherein the resistors in each set of separation electrodes are connected in series between the one or more pairs of individual electrodes.

* * * * *